(12) United States Patent
Clement

(10) Patent No.: US 8,104,433 B2
(45) Date of Patent: Jan. 31, 2012

(54) LONG-LASTING GUSTATORY AND/OR OLFACTORY AVERSION VETERINARY COMPOSITIONS FOR BEHAVIOR MODIFICATION

(75) Inventor: Richard J. Clement, Los Angeles, CA (US); Kati Clement-Frazier, legal representative, Los Angeles, CA (US)

(73) Assignee: Vet Planet, LLC, Boyds, MD (US)

( * ) Notice: Subject to any disclaimer, the term of this patent is extended or adjusted under 35 U.S.C. 154(b) by 0 days.

(21) Appl. No.: 12/499,899

(22) Filed: Jul. 9, 2009

(65) Prior Publication Data

US 2010/0016462 A1 Jan. 21, 2010

Related U.S. Application Data

(60) Provisional application No. 61/081,531, filed on Jul. 17, 2008.

(51) Int. Cl.
- A01K 37/00 (2006.01)
- A61K 49/00 (2006.01)
- A61K 9/44 (2006.01)
- A61K 8/00 (2006.01)
- A61K 8/18 (2006.01)
- A61Q 13/00 (2006.01)

(52) U.S. Cl. ..... 119/712; 424/10.4; 424/10.1; 424/10.2; 424/10.3; 512/1

(58) Field of Classification Search ............... 424/10.4, 424/10.1, 10.2, 10.3; 512/1; 119/712
See application file for complete search history.

(56) References Cited

U.S. PATENT DOCUMENTS

| 5,816,421 | A | 10/1998 | Clodfelter et al. | |
|---|---|---|---|---|
| 6,164,278 | A | 12/2000 | Nissani | |
| 6,239,191 | B1 * | 5/2001 | Wong et al. | 523/120 |
| 6,319,491 | B1 * | 11/2001 | Whipple | 424/65 |
| 6,468,554 | B1 | 10/2002 | Ichino | |
| 6,811,791 | B2 | 11/2004 | Kensek | |
| 7,332,182 | B2 | 2/2008 | Sackler | |
| 2002/0013481 | A1 * | 1/2002 | Schonrock et al. | 549/403 |
| 2003/0064099 | A1 * | 4/2003 | Oshlack et al. | 424/465 |
| 2004/0126324 | A1 | 7/2004 | Hughes | |
| 2005/0113510 | A1 * | 5/2005 | Feldstein et al. | 524/556 |
| 2005/0214351 | A1 | 9/2005 | Chew | |
| 2006/0069409 | A1 | 3/2006 | Morris | |
| 2007/0093392 | A1 | 4/2007 | Vavra et al. | |
| 2008/0008660 | A1 | 1/2008 | Rabenhorst et al. | |
| 2008/0190381 | A1 | 8/2008 | Stampe et al. | |

FOREIGN PATENT DOCUMENTS

| JP | 2000026260 | 1/2000 |
|---|---|---|
| WO | WO 2008049520 | 5/2008 |

OTHER PUBLICATIONS

Cabot Corporation CAB-O-SIL product reference (CAB-O-SIL M-5 Product Form c. 2004 pp. 1-2).*

Ethyl Alcohol Hand Book, 6th edition c. 2003, Equistar Chemicals; Lyondell Chemical Company, Houston TX.*

Ethyl Alcohol Handbook (6th ed.) {Ethyl Alcohol Handbook, 6th edition c. 2003, Equistar Chemicals; Lyondell Chemical Company, Houston TX.*

Cubero-Castillo et al., "Effect of Compounds Sequence on Bitterness Enhancement," Chem. Senses, vol. 26, (2001), pp. 419-424.

* cited by examiner

Primary Examiner — Patrick Ryan
Assistant Examiner — Aaron Greso
(74) Attorney, Agent, or Firm — Alston & Bird LLP

(57) ABSTRACT

Disclosed herein are gustatory and/or olfactory aversion compositions comprising one or more bitterants and appropriate adhesives or tackifiers, and the like, which provide a long-lasting effect. The compositions are useful for behavior modification, especially in animals, such as pets or livestock.

18 Claims, No Drawings

LONG-LASTING GUSTATORY AND/OR OLFACTORY AVERSION VETERINARY COMPOSITIONS FOR BEHAVIOR MODIFICATION

RELATED APPLICATIONS

This application claims priority to U.S. Provisional Patent Application No. 61/081,531, filed Jul. 17, 2008, the entire contents of which is hereby incorporated by reference.

BACKGROUND OF THE INVENTION

1. Field of the Invention

This invention relates to compositions useful for modifying the behavior of an animal through gustatory and/or olfactory aversion, and the uses of such compositions for this purpose.

2. Background Art

An animal having a lesion or superficial affliction, or a bandage or other foreign object, such as a medical device, on its body tends to lick or bite at the lesion or superficial affliction or molest or attempt to remove the bandage or foreign object. This behavior results in the lesion taking longer to heal or the bandage or foreign object becoming nonfunctional for its purpose.

One way this problem has been addressed in the past is by the use of head cones, also known as Elizabethan collars, to prevent the animal's access to the area with its mouth. However, head cones have many disadvantages. Often the head cone must be worn for several days, putting undue leverage and pressure on the animal's neck. Further, head cones are impractical to use if the animal must be crated in order to limit activity or is too large. For a domestic animal, enduring the physical burden and visual limitations of a head cone can easily result in the animal damaging furniture and harming itself. The unnatural circumstance of having to endure a head cone and an increased sense of vulnerability due to a reduced field of vision can increase stress levels.

Another method of addressing this problem involves the application of bitter tasting substances. One such substance is a spray sold under the tradename Bitter Apple. Another is a topical spray with an added antiseptic agent sold under the tradename Wound-Guard. A gel sold under the tradename Yuk-2e can be applied directly to the animal's wound or bandage. Yuk-2e is a combination of denatonium and sucrose octaacetate and is extremely offensive to the animal, yet harmless. In all these products, animals are dissuaded from molesting, licking, chewing or biting or self-traumatizing wounds, sutures, dressings, and the like by the bitter taste of the composition. However, none of these products provides long-lasting deterrence. Each requires relatively frequent re-application. In both veterinary and home environments, this frequent need for attention puts an undue burden on the animal's caretaker and may serve to contaminate surfaces with which the animal comes into contact.

In the past, various devices have been employed for use in discouraging animals from licking their wounds. These devices, for the most part, have been cumbersome and difficult to controllably position on the skin adjacent the wound. Furthermore, due to their large size, most prior art devices are susceptible to being removed by the animal through rubbing contact with stationary objects. An electrically actuated apparatus for discouraging animals from licking their wounds can have exposed conductive traces for completing a circuit through the animal's tongue whenever it comes in contact with adjacent conductive traces. The apparatus has been found to be particularly useful for use when pets such as dogs or cats suffer wounds, and their tendency to lick their wounds impairs prompt healing.

It would be useful to have a long-lasting gustatory and/or olfactory aversion formulation that avoids the problems of the prior art remedies discussed above.

SUMMARY OF THE INVENTION

Disclosed herein are gustatory and/or olfactory aversion compositions comprising one or more bitterants and one or more appropriate adhesives, tackifier and the like which provide a long-lasting effect. A composition as disclosed herein is useful for behavior modification, especially in animals, such as pets or livestock. Further, disclosed herein is a method of modifying the behavior of an animal using a gustatory and/or olfactory aversion composition. Preferably, the method is useful for deterring an animal from licking, chewing or biting an area or object using the gustatory and/or olfactory aversion compositions disclosed herein.

DETAILED DESCRIPTION OF THE INVENTION

Disclosed herein are compositions comprising, Gantrez® ES-225 solution; citronella; denatonium benzoate; sucrose octaacetate; quinine sulfate; naringen; a solvent; and silica. The compositions are useful for modifying the behavior of an animal. For example, the compositions are especially useful for deterring an animal from licking a particular area or object. It is particularly useful for deterring an animal from licking an area, such as a lesion, superficial affliction and the like in order to allow the area to remain unmolested or the lesion to heal.

In another embodiment, disclosed are compositions comprising, one or more bitterant(s) and one or more adhesives. These compositions can further contain excipients and rheological modifiers, all of which are well known to those of ordinary skill in the art. Preferably, these compositions are in the form of a paste, gel or spray. Methods of formulating the compositions are well known in the art.

The term "animal" means any livestock, such as cattle, horses, sheep, goats, swine, and other species as well as domesticated animals. Preferably, the animal is a domestic animal such as canine or feline. Most preferably, the animal is canine.

The term "accessible" refers to a potentially reachable or available area, space or object with which the animal may interact. Accessible does not mean that the area, space or object has to be made accessible to the animal. An area, space or object can be accessible to an animal even if the animal is restrained from interacting with the area, space or object by any means.

The term "molesting" refers to licking, chewing, biting, contacting, disturbing, befouling, sullying, contaminating and the like.

Preferred adhesives are medically acceptable adhesives, gums, glues, caulk, thickeners, tackifiers and the like. More preferably, the adhesives are dental or denture adhesives and the like. These adhesives, gums, glues and the like are well known to those of ordinary skill in the art. These include, but are not limited to, gantrez-type polymers and copolymers. Such polymers and copolymers are well known to those of ordinary skill in the art. Most preferably, the adhesive is poly(vinyl $C_{1-5}$ alkyl ether/maleic acid mono $C_{1-5}$ alkyl ester). Preferably, each $C_{1-5}$ alkyl moiety above is independently selected from methyl and ethyl. Thus, one of the most preferred adhesives is poly(vinyl methyl ether/maleic acid monoethyl ester). Gantrez is also known as Adhesyn™.

Bitterants are chemicals that are non-toxic, but can be added to a product to make it smell and/or taste bad. Useful bitterants are well known to those of skill in the art. In preferred embodiments, the one or more bitterant(s) present in the gustatory and/or olfactory aversion compositions disclosed herein is/are selected from the group consisting of denatonium, sucrose octaacetate, quinine sulfate, naringen and citronella. When denatonium is present, it can be in any useful form, such as a salt. Most preferably, it is present in its salt form as denatonium benzoate. When quinine is present, it can be in any useful form, such as a salt. Most preferably, it is present in its salt form as quinine sulfate. When more than one bitterants are used, they can be pre-mixed together before adding to the composition.

In another embodiment, disclosed herein is a method of modifying an animal's behavior. The method comprises contacting an area accessible to the animal with a composition as described herein. Specifically, disclosed is a method of deterring an animal from licking, chewing, biting, or molesting in any way, an area, the method comprising, contacting the area to be protected from the molesting, licking and the like or contacting in the vicinity thereof with a composition disclosed herein, wherein the molesting, licking and the like is deterred. The method is not limited to licking, and includes chewing, biting, or any other unwanted behavior such as molesting which can be deterred by gustatory and/or olfactory aversion. The method further comprises subsequently applying additional composition to the area to be protected. The method can further comprise prior to the first or subsequent applications of a composition disclosed herein to the area or the vicinity thereof to be protected, first contacting the animal's intra-oral surfaces, lips or nose with a gustatory and/or olfactory aversion composition. Alternatively, the area or vicinity thereof can be contacted with a composition first and then the animal's intra-oral surfaces, lips or nose can be contacted. Using the gustatory and/or olfactory aversion compositions in the manners described above can help reinforce the behavior modification.

The presently claimed gustatory and/or olfactory aversion compositions advantageously provide a long-lasting effect. Adhesives promote prolonged contact and interaction of the bitterants with the animal's taste receptors and all intra-oral surfaces thereby extending gustatory and olfactory experiences. Even the usual pytalism (hypersalivation) by the animal will not effectively dilute the bitterants' intra-oral residency time and effect. The adhesive allows the bitterant to stick to the area or the vicinity thereof to be protected as well as to the animal's intra-oral surfaces. Intra-oral surfaces include all posterior and anterior structures associated with the mouth, including, lips, gums, teeth, palate, uvula and tongue. This feature is unlike prior art compositions, which have to be re-applied frequently. Further, this feature results in the animal safely sensing by taste, smell or mouth-feel the composition for a longer period. Thus, the animal continues to sense the bitterant longer. The extended time the bitterant is sensed results in the animal more likely remembering the strong deterrent or associating the behavior, i.e. molesting, licking, and the like with the bitterant. Thus, the long-lasting gustatory and/or olfactory aversion composition provides advantages for behavior modification.

The area which the animal is being deterred from molesting, licking, chewing, biting and the like can be any area amenable to contacting with a composition disclosed herein. The area does not need to be on the animal's body. The method covers any area accessible, reachable or available to the animal which can be a part or on the animal's body or can be a separate area that the animal can access or reach. Non-limiting examples of these areas include furniture and walls. However, the compositions disclosed herein are particularly useful for deterring an animal from molesting, licking and the like a lesion or superficial affliction on its body so that the lesion or superficial affliction can properly heal. The lesion or superficial affliction can be any cut or wound, including burns, abrasions, surgical incisions, including sutures, dressings, allergic reaction, bites, sores, broken skin, and the like and "hot spots." More preferably, the compositions are applied adjacent to the area to be protected. This includes the fur or skin at or adjacent to the outer edge of the lesion, superficial affliction, foreign object and the like and extending out as far as necessary to deter molesting, licking and the like of the area to be protected. The area in vicinity thereof also includes any bandage or dressing that can cover the area, e.g. a bandage covering at least a portion of the lesion, etc. The area can also include a device on the animal that would benefit from the animal not licking or molesting it. Examples of such devices are indwelling catheters of any kind.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLES

Example 1

Formulation of Yuk Forte

A formulation of Yuk Forte anti-lick was prepared using the ingredients and ratios listed in Table 1.

TABLE 1

| Ingredient | Wt, g | % w/w |
|---|---|---|
| 1. Gantrez ® ES-225 soln. | 418.08 | |
| Gantrez ® ES-226 | 230.60 | 39.86 |
| Ethanol | 214.48 | 47.24 |
| 2. Citronella | 38.26 | 7.49 |
| 3. 3723-5A | 30.61 | |
| Denatonium benzoate | 1.07 | 0.21 |
| Sucrose octaacetate | 1.09 | 0.21 |
| Qunine sulfate | 1.08 | 0.21 |
| naringen | 0.53 | 0.10 |
| Ethanol | 26.83 | |
| 4. Fumed silica | 23.90 | 4.68 |
| Total Wt, g | 510.85 | |
| Total % w/w | | 100.00 |

The above-listed ingredients are specifically: Gantrez® ES-225 solution—poly(vinyl methyl ether/maleic acid monoethyl ester) copolymer, % solids=48.7, ISP Lot 03400118639; Citronella—approx. 90%, Spectrum Lot No. RP0474; Denatonium benzoate, NF—Spectrum Lot Nos. SB0033/RG0830; sucrose octaacetate, NF—Spectrum Lot No. TC1832; Quinine sulfate, dehydrate, USP—Spectrum Lot No. TD1481; Naringin, Spectrum Lot No. TD1250; Ethanol—dehydrated alcohol, 200 proof, USP, Spectrum Lot No. TU0974; Fumed silica—Cab-O-Sil® M-5P amorphous fumed silica; Cabot Lot No. 302465.

It will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A composition consisting essentially of:
   i) a copolymer of monoalkyl esters of poly (methyl vinyl ether/maleic acid);
   ii) citronella;
   iii) denatonium benzoate;
   iv) sucrose octaacetate;
   v) quinine sulfate;
   vi) naringen;
   vii) a solvent; and
   viii) fumed silica.

2. The composition of claim 1, wherein said solvent is ethanol.

3. A composition comprising:
   i) one or more bitterant(s), wherein said bitterant(s) is/are present in an amount of not more than about 9% w/w and not less than about 0.10% w/w; and
   ii) at least one adhesive,
   wherein said at least one adhesive is a dental adhesive consisting essentially of a copolymer of methylvinyl ether and maleic anhydride and/or acid.

4. The composition of claim 3, wherein said one or more bitterant(s) is selected from the group consisting of denatonium, sucrose octaacetate, quinine, naringen and citronella.

5. The composition of claim 3, wherein said one or more bitterant(s) comprises denatonium benzoate, sucrose octaacetate, quinine sulfate, naringen and citronella.

6. The compound of claim 3, wherein said copolymer is poly(vinyl $C_{1-5}$ alkyl ether/maleic acid mono $C_{1-5}$ alkyl ester).

7. The compound of claim 3, wherein said copolymer is poly(vinyl methyl ether/maleic acid monoethyl ester).

8. A method of deterring an animal from licking an area, comprising:
   i) contacting said area or in the vicinity thereof with the composition of claim 3, wherein said licking is deterred.

9. The method of claim 8, wherein said animal is a domestic animal.

10. The method of claim 9, wherein said domestic animal is a canine.

11. The method of claim 8, wherein said area is a lesion or superficial affliction.

12. The method of claim 8, wherein said contacting in the vicinity thereof comprises contacting one or more site(s) adjacent to said area.

13. The method of claim 12, wherein said site(s) comprises the outer edge of said area.

14. The method of claim 8, wherein said contacting in the vicinity thereof comprises contacting a bandage or occlusive material covering at least a portion of said area.

15. The method of claim 8, further comprising, prior to i), contacting said animal's intra-oral surface(s), lips or nose with said composition.

16. The method of claim 8, further comprising, after i), contacting said animal's intra-oral surface(s), lips or nose with said composition and/or subsequently contacting said area or in the vicinity thereof with said composition.

17. A method of modifying an animal's behavior, comprising contacting an area accessible to said animal with a composition of claim 3.

18. A method of deterring an animal from molesting an area, comprising:
   i) contacting said area or in the vicinity thereof with the composition of claim 1, wherein said molesting is deterred.

* * * * *